(12) United States Patent
Goldstein et al.

(10) Patent No.: US 7,196,097 B2
(45) Date of Patent: Mar. 27, 2007

(54) 6-ALKOXY-PYRIDO-PYRIMIDINES

(75) Inventors: David Michael Goldstein, San Jose, CA (US); Julie Anne Lim, San Mateo, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/503,697

(22) Filed: Aug. 14, 2006

(65) Prior Publication Data

US 2006/0276646 A1 Dec. 7, 2006

Related U.S. Application Data

(62) Division of application No. 10/634,936, filed on Aug. 5, 2003, now Pat. No. 6,965,030.

(60) Provisional application No. 60/401,491, filed on Aug. 6, 2002.

(51) Int. Cl.
*A01N 43/42* (2006.01)
(52) U.S. Cl. .................. 514/299; 544/279; 546/122
(58) Field of Classification Search ................ 514/299; 544/279; 546/122
See application file for complete search history.

(56) References Cited

U.S. PATENT DOCUMENTS

| | | | |
|---|---|---|---|
| 4,215,216 A | 7/1980 | Scotese et al. | |
| 5,037,826 A | 8/1991 | Blythin et al. | |
| 5,620,981 A | 4/1997 | Blankley et al. | |
| 5,733,913 A | 3/1998 | Blankley et al. | |
| 5,945,422 A | 8/1999 | Doherty et al. | |
| 6,150,359 A * | 11/2000 | Barvian et al. | 514/234.5 |
| 6,316,464 B1 * | 11/2001 | Cheng et al. | 514/300 |
| 6,451,804 B1 * | 9/2002 | Dunn et al. | 514/262.1 |
| 6,506,749 B2 * | 1/2003 | Chen et al. | 514/234.2 |
| 6,518,276 B2 * | 2/2003 | Arzeno et al. | 514/264.11 |
| 6,809,199 B2 * | 10/2004 | Doherty et al. | 544/256 |
| 2002/0055513 A1 | 5/2002 | Arzeno et al. | |

FOREIGN PATENT DOCUMENTS

| | | |
|---|---|---|
| EP | 0 278 686 A1 | 8/1988 |
| EP | 0 790 997 B1 | 3/2000 |
| WO | WO 93/17682 | 9/1993 |
| WO | WO 96/34667 | 11/1996 |
| WO | WO 98/33798 | 8/1998 |
| WO | WO 99/61444 | 12/1999 |
| WO | WO 01/29041 A1 | 4/2001 |
| WO | WO 02/064594 A2 | 8/2002 |
| WO | WO 03/062236 A1 | 7/2003 |

OTHER PUBLICATIONS

Boschelli, et al, "Synthesis and Tyrosine Kinase Inhibitory Activity of a Series of 2-Amino-8H-pyrido[2,3-d]pyrimidines. Identification of Potent, Selective Platelet-Derived Growth Factor Receptor Tyrosine Kinase Inhibitors," *Journal of Med. Chem.*, (1998), pp. 4365-4377, vol. 41.

Klutchko, et al., "2-Substituted Aminopyrido[2,3-d] pyrimidin-7(8H)-ones. Structure-Activity Relationships Against Selected Tyrosine Kinases and in Vitro and in Vivo Anticancer Activity," *Journal of Med. Chem.*, (1998), pp. 3276-3292, vol. 41.

Barvian, et al., "Pyrido[2,3-d]pyrimidin-7-one Inhibitors of Cyclin-Dependent Kinases," *Journal of Med. Chem.*, (2000), pp. 4606-4616, vol. 43.

Hamby, et al., "Structure-Activity Relationships for a Novel Series of Pyrido[2,3-d]pyrimidine Tyrosine Kinase Inhibitors," *Journal Med. Chem.*, (1997), pp. 2296-2303, vol. 40.

Boehm and Adams, "New Inhibitors of p38 kinase," *Expert Opinion on Therapeutic Patents*, vol. 10:1 (2000), pp. 25-37.

Trumpp-Kallmeyer, et al., Development of a Binding Model to Protein Tyrosine Kinases for Substituted Pyrido[2,3-d]pyrimidine Inhibitors, *J. Medicinal Chemistry*, vol. 41 (1998), pp. 1752-1763.

\* cited by examiner

*Primary Examiner*—Thurman Page
*Assistant Examiner*—Chukwuma Nwaonicha
(74) *Attorney, Agent, or Firm*—Grant D. Green

(57) ABSTRACT

The present invention provides compounds of the Formula I:

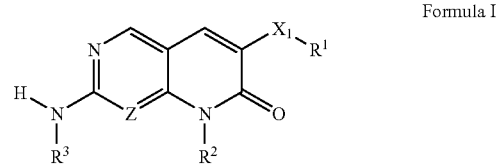

Formula I wherein $R^1$ is alkyl, cycloalkyl, cycloallkylalkyl, or —$CH_2$-alkenyl, $X^1$ is O, NH, N(alkyl), S or —C(=O), Z is N or CH; and $R^2$ and $R^3$ are as defined herein, pharmaceutical compositions comprising same, and methods for their use.

10 Claims, No Drawings

6-ALKOXY-PYRIDO-PYRIMIDINES

RELATED APPLICATIONS

This application claims the benefit of U.S. Ser. No. 11/121,862, filed May 4, 2005, which is a division of U.S. Ser. No. 10/634,936, filed Aug. 5, 2003, now U.S. Pat. No. 6,965,030, based on U.S. Ser. No. 60/401,491, filed Aug. 6, 2002, the contents of which are incorporated herein by reference.

FIELD OF THE INVENTION

The present invention relates to pyridopyrimidines and derivatives thereof. In particular, the present invention provides 2,6-disubstituted 7-oxo-pyrido[2,3-d]pyrimidines, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin, and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpes virus-7 (HHV-7), human herpes virus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis, and atopic dermatitis. *J. Exp. Opin. Ther. Patents*, (2000), Vol. 10(1).

The inhibition of these cytokines by inhibition of the p38 kinase is of benefit in controlling, reducing, and alleviating many of these disease states.

Certain 6-aryl-pyrido[2,3-d]pyrimidin-7-ones, -7-imines and -7-thiones are disclosed as inhibitors of protein tyrosine kinase mediated cellular proliferation in WO 96/34867, published Nov. 7, 1996 (Warner Lambert). Other 6-aryl-pyrido[2,3-d]pyrimidines and naphthyridines are also disclosed as inhibitors of tyrosine kinase in WO 96/15128, published May 23, 1996 (Warner Lambert). 6-alkyl-pyrido [2,3-d]pyrimidin-7-ones are disclosed as inhibitors of cyclin-dependent kinases in WO 98/33798, published Aug. 6, 1998 (Warner Lambert). Certain 4-amino-pyridopyrimidines are disclosed as inhibitors of dihydrofolate reductase in EP 0 278 686A1, published Aug. 8, 1988 (Wellcome Foundation). Compounds that are inhibitors of p38 kinase are disclosed in the following patents and patent applications, having common inventors herewith and assigned to the present assignee: U.S. Pat. No. 6,316,464, U.S. Pat. No. 6,451,804, U.S. Pat. No. 6,506,749, U.S. Pat. No. 6,518,276B2, U.S. application Ser. No. 09/693,364 (WO 01/29042), and U.S. application Ser. No. 10/073,845 (WO 02/64594).

Each of the patents, patent applications and publications referenced in this specification are incorporated herein by reference.

SUMMARY OF THE INVENTION

One aspect of the present invention provides compounds represented by Formula I:

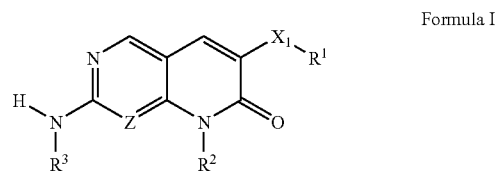

Formula I and pharmaceutically acceptable salts, hydrates, or prodrugs thereof, wherein:

Z is N or CH;

$X^1$ is O, S, C(=O), or $NR^4$ (where $R^4$ is hydrogen or alkyl);

$R^1$ is alkyl, cycloalkyl, cycloalkylalkyl, or —$CH_2$-alkenyl;

$R^2$ is hydrogen, alkyl, cycloalkyl, cycloalkylalkyl, aryl, aralkyl, haloalkyl, heteroalkyl, cyanoalkyl, alkylene-C(O)—$R^{21}$ (where $R^{21}$ is hydrogen, alkyl, hydroxy, alkoxy, amino, monoalkylamino or dialkylamino), amino, monoalkylamino, dialkylamino, acyl, or $NR^{22}$—Y—$R^{23}$ (where Y is —C(O), —C(O)O—, —C(O)$NR^{24}$, $S(O)_2$ or $S(O)_2NR^{25}$; $R^{22}$, $R^{24}$ and $R^{25}$ are independently hydrogen or alkyl; and $R^{23}$ is hydrogen, alkyl, cycloalkyl, cycloalkylalkyl, heteroalkyl or optionally substituted phenyl); and $R^3$ is alkyl, haloalkyl, aryl, aralkyl, heteroaryl, heteroaralkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl, or -heterocycloamino-$SO_2$—$R^{12}$ (where $R^{12}$ is haloalkyl, aryl, aryalkyl, heteroaryl or heteroaralkyl).

Another aspect of the present invention provides a pharmaceutical formulation comprising a Compound of Formula I and a pharmaceutically acceptable carrier, diluent, or excipient therefor.

Compounds of Formula I and their aforementioned salts are inhibitors of protein kinases and exhibit effective activity against p38 in vivo. They are also selective against p38 kinase relative to cyclin-dependent kinases and tyrosine kinases. Therefore, compounds of the present invention can be used for the treatment of diseases mediated by the pro-inflammatory cytokines such as TNF and IL-1. Thus, another aspect of the present invention provides a method for treating p38 mediated diseases or conditions in which a therapeutically effective amount of a Compound of Formula I is administered to a patient in need of such treatment.

DEFINITIONS

Unless otherwise stated, the following terms used in the specification and claims have the meanings given below:

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical —NR'C(O)R, where $R^1$ is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethylcarbonylamino, benzoylamino, benzylcarbonylamino, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

Thus, when reference is made herein to the group —$CH_2$—R, where R is an alkenyl radical as defined herein, this reference includes without limitation groups such as (—$CH_2$—CH=$CH_2$), (—$CH_2$—CH=CH—$CH_3$) and the like.

"Alkoxy" means a radical —OR where R is an alkyl as defined herein e.g., methoxy, ethoxy, propoxy, butoxy and the like.

"Alkyl" means a linear saturated monovalent hydrocarbon radical of one to eight carbon atoms or a branched saturated monovalent hydrocarbon radical of three to eight carbon atoms, e.g., methyl, ethyl, propyl, 2-propyl, n-butyl, iso-butyl, tert-butyl, pentyl, and the like. Preferably, the alkyl group is a linear alkyl of one to six carbon atoms or a branched alkyl of three to six carbon atoms, more preferably a linear alkyl of one to four carbon atoms or a branched alkyl of three or four carbon atoms.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylthio" means a radical —SR where R is an alkyl as defined above e.g., methylthio, ethylthio, propylthio, butylthio, and the like.

"Aryl" means a monovalent monocyclic or bicyclic aromatic hydrocarbon radical which is optionally substituted independently with one or more substituents, preferably one, two, or three substituents preferably selected from the group consisting of alkyl, hydroxy, alkoxy, haloalkyl, haloalkoxy, alkylthio, alkylsulfinyl, alkylsulfonyl, —$SO_2$NR'R" (where R' and R" are independently hydrogen or alkyl), Y—C(O)—R (where Y is absent or an alkylene group and R is hydrogen, alkyl, haloalkyl, haloalkoxy, hydroxy, alkoxy, amino, monoalkylamino or dialkylamino), heteroalkyl, heteroalkyloxy, heteroalkylamino, halo, nitro, cyano, amino, monoalkylamino, dialkylamino, alkylsulfonylarnino, heteroalkylsulfonylamino, sulfonamido, methylenedioxy, ethylenedioxy, heterocyclyl and/or heterocyclylalkyl. More specifically the term aryl includes, but is not limited to, phenyl, chlorophenyl, methoxyphenyl, 2-fluorophenyl, 2,4-difluorophenyl, 1-naphthyl, 2-naphthyl, and the derivatives thereof.

"Aryloxy" means a radical —OR where R is an aryl as defined herein e.g. phenoxy.

"Aryloxycarbonyl" means a radical R—C(=O)— where R is aryloxy, e.g. phenoxycarbonyl.

"Cycloalkyl" refers to a saturated monovalent cyclic hydrocarbon radical of three to seven ring carbons e.g., cyclopropyl, cyclobutyl, cyclohexyl, 4-methyl-cyclohexyl, and the like.

"Cycloalkylalkyl" means a radical —$R^aR^b$ where $R^a$ is an alkylene group and $R^b$ is cycloalkyl group as defined herein, e.g., cyclohexylmethyl, and the like.

"Substituted cycloalkyl" means a cycloalkyl radical as defined herein with one, two or three (preferably one) ring hydrogen atoms are independently replaced by cyano or —Y—C(O)R (where Y is absent or an alkylene group and R is hydrogen, alkyl, haloalkyl, hydroxy, alkoxy, amino, monoalkylamino, dialkylamino, or optionally substituted phenyl).

"Dialkylamino" means a radical —NRR' where R and R' independently represent an alkyl, hydroxyalkyl, cycloalkyl, or cycloalkylalkyl group as defined herein. Representative examples include, but are not limited to dimethylamino, methylethylamino, di(1-methylethyl)amino, (methyl)(hydroxymethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl) amino, and the like.

"Halo" means fluoro, chloro, bromo, or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl radical as defined herein wherein one, two or three hydrogen atoms have been replaced with a substituent independently selected from the group consisting of —$OR^a$, —$N(O)_mR^bR^c$, (wherein m is 0 or 1), and —$S(O)_nR^d$ (where n is an integer from 0 to 2), with the understanding that the point of attachment of the heteroalkyl radical is through a carbon atom, wherein $R^a$ is hydrogen, acyl, alkoxycarbonyl, alkyl, cycloalkyl, or cycloalkylalkyl; $R^b$ and $R^c$ are independently of each other hydrogen, acyl, alkoxycarbonyl, alkyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl, provided however, when m is 1, then $R^b$ and $R^c$ are both independently selected from alkyl, cycloalkyl and cycloalkylalkyl; and when n is 0, $R^d$ is hydrogen, alkyl, cycloalkyl, cycloalkylalkyl or optionally substituted phenyl, and when n is 1 or 2, $R^d$ is alkyl, cycloalkyl, cycloallkylalkyl, optionally substituted phenyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroalkylcarbonyl" means the group $R_a$—C(=O)—, where $R_a$ is a heteroalkyl group. Representative examples include acetyloxymethylcarbonyl, aminomethylcarbonyl, 4-acetyloxy-2,2-dimethyl-butan-2-oyl, 2-amino-4-methyl-pentan-2-oyl, and the like.

"Heteroalkyloxy" means the group $R_a$—O—, where $R_a$ is a heteroalkyl group.

Representative examples include (Me-C(=O)—O—CH$_2$—O—, and the like.

"Heteroalkyloxycarbonyl" means the group $R_a$—C(=O), where $R_a$ is a heteroalkyloxy group. Representative examples include 1-acetyloxy-methoxycarbonyl (Me-C(=O)—O—CH$_2$—O—C(=O)—) and the like.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, heteroalkyl, hydroxy, alkoxy, halo, nitro or cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heteroaralkyl" means a radical —$R^aR^b$ where $R^a$ is an alkylene group and $R^b$ is a heteroaryl group as defined herein, e.g., pyridin-3-ylmethyl, imidazolylethyl, pyridinylethyl, 3-(benzofuran-2-yl)propyl, and the like.

"Heteroalkylsubstituted cycloalkyl" means a cycloalkyl radical as defined herein wherein one, two or three hydrogen atoms in the cycloalkyl radical have been replaced with a heteroalkyl group with the understanding that the heteroalkyl radical is attached to the cycloalkyl radical via a carbon-carbon bond. Representative examples include, but are not limited to, 1-hydroxymethylcyclopentyl, 2-hydroxymethylcyclohexyl, and the like.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, oxo (C=O), imino, hydroximino (=NOH), NR'SO$_2$R$^d$ (where R' is hydrogen or alkyl and R$^d$ is alkyl, cycloalkyl, hydroxyalkyl, amino, monoalkylamino or dialkylamino), —X—Y—C(O)R (where X is O or NR', Y is alkylene or absent, R is hydrogen, alkyl, haloalkyl, alkoxy, amino, monoalkylamino, dialkylamino, or optionally substituted phenyl, and R' is H or alkyl), or —S(O)$_n$R (where n is an integer from 0 to 2) such that when n is 0, R is hydrogen, alkyl, cycloalkyl, cycloalkylalkyl optionally substituted phenyl or thienyl, and when n is 1 or 2, R is alkyl, cycloalkyl, cycloalkylalkyl, optionally substituted phenyl, thienyl, amino, acylamino, monoalkylamino or dialkylamino. Representative examples include, but are not limited to, 2-, 3-, or 4-hydroxycyclohexyl, 2-, 3-, or 4-aminocyclohexyl, 2-, 3-, or 4-methanesulfonamido-cyclohexyl, and the like, preferably 4-hydroxycyclohexyl, 3,5-dihydroxy-cyclohexyl, 2-aminocyclohexyl or 4-methanesulfonamido-cyclohexyl.

"Heterosubstituted cycloalkyl-alkyl" means a radical $R^aR^b$—where $R^a$ is a heterosubstituted cycloalkyl radical and $R^b$ is an alkylene radical.

"Heterocycloamino" means a saturated monovalent cyclic group of 4 to 8 ring atoms, wherein one ring atom is N and the remaining ring atoms are C. Representative examples include piperidine and pyrrolidine.

"Heterocyclyl" means a saturated or unsaturated non-aromatic cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyano, cyanoalkyl, hydroxy, alkoxy, amino, monoalkylamino, dialkylamino, aralkyl, —(X)$_n$—C(O)R (where X is O or NR', n is 0 or 1, R is hydrogen, alkyl, haloalkyl, hydroxy (when n is 0), alkoxy, amino, monoalkylamino, dialkylamino, or optionally substituted phenyl, and R' is H or alkyl), -alkylene-C(O)R$^a$ (where R$^a$ is alkyl, OR or NR'R" and R is hydrogen, alkyl or haloalkyl, and R' and R' are independently hydrogen or alkyl), or —S(O)$_n$R (where n is an integer from 0 to 2) such that when n is O, R is hydrogen, alkyl, cycloalkyl, or cycloalkylalkyl, and when n is 1 or 2, R is alkyl, cycloalkyl, cycloalkylalkyl, amino, acylamino, monoalkylamino, dialkylamino or heteroalkyl. More specifically the term heterocyclyl includes, but is not limited to, tetrahydropyranyl, piperidino, N-methylpiperidin-3-yl, 2-oxo-piperidinyl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof.

"Heterocyclylalkyl" means a radical —$R^aR^b$ where $R^a$ is an alkylene group and $R^b$ is a heterocyclyl group as defined above, e.g., tetrahydropyran-2-ylmethyl, 2- or 3-piperidinylmethyl, 3-(4-methyl-piperazin-1-yl)propyl and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl, 1,5-dihydroxy-pent-3-yl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Monoalkylamino" means a radical —NHR where R is an alkyl, hydroxyalkyl, cycloalkyl, or cycloalkylalkyl group as defined above, e.g., methylamino, (1-methylethyl)amino, hydroxymethylamino, cyclohexylamino, cyclohexylmethylamino, cyclohexylethylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy, and acyl.

"Pharmaceutically acceptable excipient" means an excipient that is useful in preparing a pharmaceutical composition that is generally safe, non-toxic and neither biologically nor otherwise undesirable, and includes excipients that are acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, or sulfhydryl group, respectively. Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1–92, Elesevier, New York-Oxford (1985).

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

DETAILED DESCRIPTION

Though the broadest description of the invention is set forth in the Summary of the Invention, particular aspects are set forth below.

One aspect of the present invention provides a compound of Formula I:

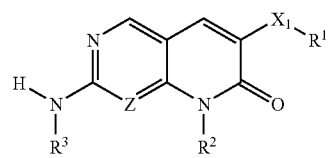

Formula I where $R^1$, $R^2$, Z and $X^1$, are as defined above.

Preferably, Z is N.

Preferably, $X^1$ is O, S or C=O, more preferably O.

Preferably, $R^1$ is alkyl. More preferably, $R^1$ is ethyl.

Preferably, $R^2$ is alkyl, aryl, cycloalkyl or heteroalkyl, more preferably methyl or hydroxyalkyl.

Preferably $R^3$ is cycloalkyl, cycloalkylalkyl, heteroalkyl-substituted cycloalkyl, heterosubstituted cycloalkyl, heteroalkyl, heterocyclyl or heterocyclylalkyl. More preferably, $R^3$ is cycloalkyl, heteroalkylsubstituted cycloalkyl, heterosubstituted cycloalkyl, heteroalkyl or heterocyclyl. When $R^3$ is heteroalkyl, particularly preferred examples of heteroalkyl $R^3$ groups are hydroxyalkyl and/or alkoxyalkyl, e.g. (1-hydroxy-2-methyl)-prop-2-yl, 1-hydroxy-pentan-2-yl, (S)-2-hydroxy-1,2-dimethyl-propyl, (R)-2-hydroxy-1,2-dimethyl-propyl, (S)-2-hydroxy-1-methyl-ethyl, 1-hydroxymethyl-cyclopentan-1-yl, 2-hydroxy-2-methyl-propyl, and 3-methoxy-1(2-methoxy-ethyl)propyl. Particularly preferred examples of heterocyclyl $R^3$ include tetrahydro-2H-pyran-4-yl, 1-(methylsulfonyl)piperidin-4-yl, 1-carboxyethyl)piperidin-4-yl, 1,1-dioxidotetrahydro-2H-thiopyran-4-yl, and morpholinyl.

According to another aspect of the invention, preferred compounds of the invention are compounds of Formula (1), above, in which $R^3$ is selected from 4-hydroxycyclohexyl, tetrahydro-2H-pyran-4-yl, 1-(methylsulfonyl)piperidin-4-yl, cyclopentyl, (S)-(2-hydroxy-1,2-dimethyl)propyl, 2,2- diethoxyethyl, 2,2-dimethoxyethyl, 3-hydroxypyridin-2-yl, (S)-(1-hydroxymethyl-2-methyl)propyl, 4-(2-(N,N-diethylamino)ethoxy)phenyl, benzyl, phenyl, butyl, dodecyl, 2-hydroxyethyl, 3-methylbutyl, 2-methylpropyl, (2-hydroxy-1,1-dimethyl)ethyl, 2,3,-dihydroxypropyl, 3-hydroxypropyl, hexyl, pyridin-2-yl, 2-morpholinoethyl, 2-(piperidin-1-yl) ethyl, cyclohexylmethyl, 1-(hydroxymethyl)butyl, 4-fluorophenyl, cyclopropylmethyl, 2-methoxyethyl, 3-(N,N-dimethylamino)propyl, isopropyl, methyl, 3-furylmethyl, 1-oxidotetrahydro-2H-thiopyran-4-yl, 1,1-dioxidotetrahydro-2H-thiopyran-4-yl, 1-phenylpropyl, phemethyl, 4-(2-hydroxyethyl)phenyl, 3-(4-methylpiperazin-1-yl)propyl, 4-hydroxybutyl, 3-morpholinopropyl, 3-(2-pyrrolidinon-1-yl)propyl, 2-acetamidoethyl, 2-(pyridin-2-yl)ethyl, pentyl, 2-(N,N-dimethylamino)ethyl, 2-(pyrrolidin-1-yl)ethyl, 3-(pyrrolidin-1-yl)propyl, ethyl, 5-methylpyridin-2-yl, propyl, methyl, cyclopropyl, (1-hydroxymethyl-3-methylthio) propyl, (1-hydroxymethyl)cyclpentyl, 1,1-dimethylpropyl, 3-ethoxy-3-oxo-propyl, 3-methoxypropyl, cylcobutyl, 1-(oxo-ethoxymethyl)piperidin-4-yl, 4-methoxycyclohexyl, 3,5-dihydroxy-cyclohexyl, 2-cyclohexylethyl, (2-methylthiazol-5-yl)methyl, imidazo[2,1-b]thiazol-6-ylmethyl, 4-phenylbutyl, 2-(4-aminophenyl)ethyl, pyridin-3-yl, tetrahydro-2H-thiopyran-4-yl, and (1-hydroxymethyl)butyl.

Other combinations of preferred groups, and/or particularly preferred groups, may form still other groups of preferred compounds.

For example, another group of preferred compounds are compounds having the Formula (I"),

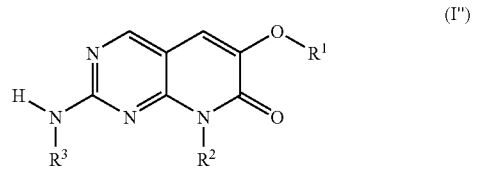

wherein $R^1$ is alkyl, more preferably ethyl; $R^2$ is selected from hydrogen, alkyl, aryl, cycloalkyl and heteroalkyl (more preferably methyl or hydroxyalkyl), and $R^3$ is heteroalkyl or heterocyclyl. Even more preferred are compounds of Formula (I"), as immediately defined above, wherein $R^1$ and $R^2$ are selected from those groups recited immediately above, and $R^3$ is selected from (1-hydroxy-2-methyl)-prop-2-yl, 1-hydroxy-pentan-2-yl, (s)-2-hydroxy-1,2-dimethyl-propyl, (R)-2-hydroxy-1,2-dimethyl-propyl, (S)-2-hydroxy-1-methyl-ethyl, 1-hydroxymethyl-cyclopentan-1-yl, 2-hydroxy-2-methyl-propyl, 3-methoxy-1(2-methoxy-ethyl) propyl, tetrahydro-2H-pyran-4-yl, 1-(methylsulfonyl) piperidin-4-yl, 1-carboxyethyl)piperidin-4-yl, 1,1-dioxidotetrahydro-2H-thiopyran-4-yl, and morpholinyl. Even further preferred are compounds where $R^1$ is ethyl, $R^2$ is methyl, and $R^3$ is (1-hydroxy-2-methyl)-prop-2-yl, 1-hydroxy-pentan-2-yl, (S)-2-hydroxy-1,2-dimethyl-propyl, (R)-2-hydroxy-1,2-dimethyl-propyl, (S)-2-hydroxy-1-methyl-ethyl, 1-hydroxymethyl-cyclopentan-1-yl, 2-hydroxy-2-methyl-propyl, 3-methoxy-1(2-methoxy-ethyl)propyl, tetrahydro-2H-pyran-4-yl, 1-(methylsulfonyl)piperidin-4-yl, 1-carboxyethyl)piperidin-4-yl, 1,1-dioxidotetrahydro-2H-thiopyran-4-yl, and morpholinyl.

Still another group of preferred compounds are those having the formula,

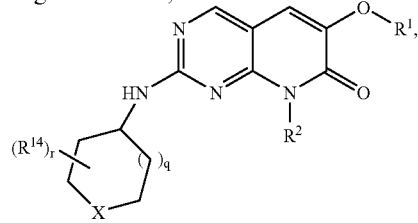

wherein $R^1$ and $R^2$ are defined as above, X is —O—, —C(=O)—, —N($R^{12a}$)—, or —CH($R^{12b}$)—; $R^{12a}$ is selected from hydrogen, $C_{1-4}$alkyl, —C(=O)$R^{15}$, —C(O)$_2$$R^{15}$, and —S(O)$_2$($C_{1-4}$alkyl); $R^{12b}$ is selected from hydrogen, $C_{1-4}$alkyl, —O$R^5$, —C(=O)$R^{15}$, —C(O)$_2$$R^{15}$, and —S(O)$_2$($C_{1-4}$alkyl); $R^{14}$ is selected from $C_{1-4}$alkyl, oxo (=O), —O$R^{15}$, —C(=O)$R^{15}$, —C(O)$_2$$R^{15}$, and —S(O)$_2$($C_{1-4}$alkyl); $R^{15}$ is at each occurrence independently selected from each other $R^{15}$ from hydrogen and $C_{1-4}$alkyl; q is 0 or 1; and r is 0, 1 or 2.

Within this group of preferred compounds, more preferred are those compounds wherein X is —N($R^{12a}$)—, and $R^{12a}$ is —S(O)$_2$($C_{1-4}$alkyl).

The compounds of the present invention can exist in unsolvated forms as well as solvated forms, including hydrated forms. In general, the solvated forms, including hydrated forms, are equivalent to unsolvated forms and are intended to be encompassed within the scope of the present invention. In addition to the compounds described above, the compounds of the present invention include all tautomeric forms. Furthermore, the present invention also includes all pharmaceutically acceptable salts of those compounds along with prodrug forms of the compounds and all stereoisomers whether in a pure chiral form or a racemic mixture or other form of mixture.

The compounds of Formula I are capable of further forming pharmaceutically acceptable acid addition salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1–19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

While the forms of the invention herein constitute presently preferred embodiments, many others are possible. It is not intended herein to mention all of the possible equivalent forms or ramifications of the invention. It is understood that the terms used herein are merely descriptive rather than limiting, and that various changes can be made without departing from the spirit or scope of the invention.

Abbreviations

The following Abbreviations are used in the Methods of Preparation and Examples herein for ease of reference:

EtOH=ethanol
MeOH=methanol
DCE=dichloroethane
DCM=dichloromethane
EtOAc=ethyl acetate
Sat'd=saturated
THF=tetrahydrofuran
MP or Mp=melting point Processes for Preparing the Compounds The compounds of the present invention can be prepared by a variety of methods. In one aspect of the present invention, method for preparing compounds of Formula I' wherein Z is N, are shown in Schemes 1 and 4 below. A method of making compounds of Formula I, wherein $R^2$ is an amino group is shown in Scheme 2. Methods of making compounds of Formula I", wherein Z is CH, are shown in Schemes 3 and 3A.

It should be appreciated that although the Schemes often indicate exact structures, methods of the present invention apply widely to analogous compounds of Formula I, given appropriate consideration to protection and deprotection of reactive functional groups by methods standard to the art of organic chemistry. For example, hydroxy groups, in order to prevent unwanted side reactions, sometimes need to be converted to ethers or esters during chemical reactions at other sites in the molecule. The hydroxy protecting group is then removed to provide the free hydroxy group. Similarly, amino groups and carboxylic acid groups can be derivatized to protect them against unwanted side reactions. Typical protecting groups, and methods for attaching and cleaving them, are described fully in the above incorporated references by T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1–8 (John Wiley and Sons, 1971–1996).

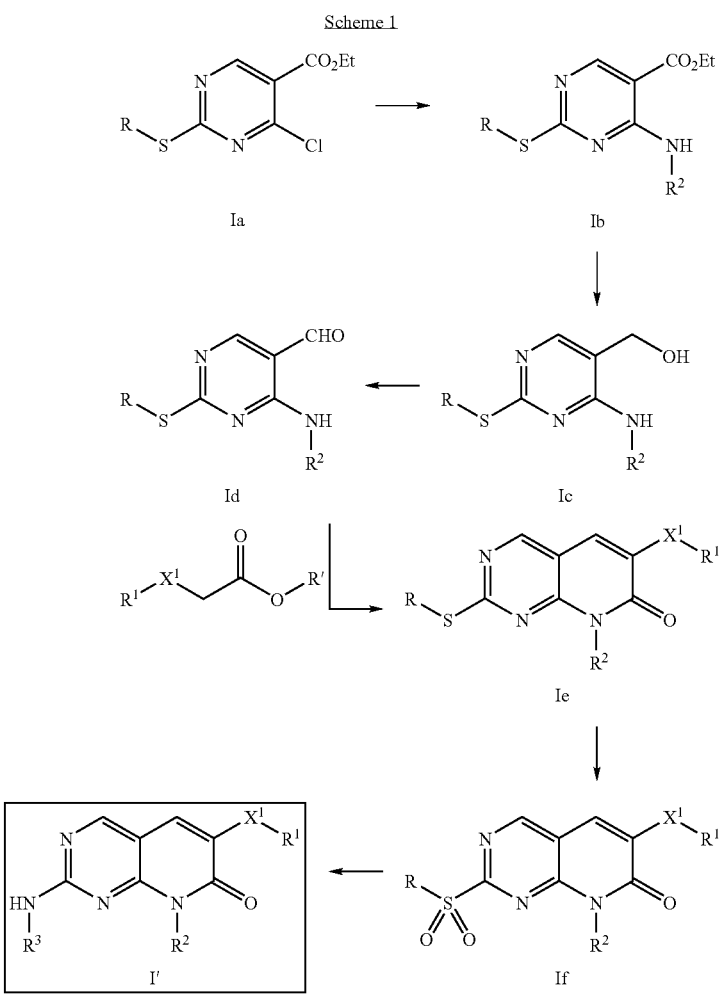

Treatment of a compound of Formula Ia with a primary amine ($R^2$—$NH_2$) provides a compound of Formula Ib. This reaction is conveniently carried out in a solvent which is inert under the reaction conditions, preferably a halogenated aliphatic hydrocarbon, especially DCM, an optionally halogenated aromatic hydrocarbon, or an open-chain or cyclic ether such as THF, a formamide or a lower alkanol. Suitably, the reaction is carried out at about −20° C. to about 120° C.

Reduction of a compound of Formula Ib provides an alcohol of Formula Ic. This reduction is typically carried out using lithium aluminum hydride in a manner well known to those of skill in the art (e.g., in a solvent which is inert under the conditions of the reduction, preferably an open-chain or cyclic ether, especially THF, at about −20° C. to about 70° C., preferably at about 0° C. to about room temperature).

Oxidation of an alcohol of Formula Ic provides a carboxaldehyde of Formula Id. The oxidation is typically carried out with manganese dioxide, although numerous other methods can also be employed (see, for example, ADVANCED ORGANIC CHEMISTRY, $4^{TH}$ ED., March, John Wiley & Sons, New York (1992)). Depending on the oxidizing agent employed, the reaction is carried out conveniently in a solvent which is inert under the specific oxidation conditions, preferably a halogenated aliphatic hydrocarbon, especially DCM, or an optionally halogenated aromatic hydrocarbon. Suitably, the oxidation is carried out at about 0° C. to about 60° C.

Reaction of a carboxaldehyde of Formula Id with an ester, $R^1$—$X^1CH_2$—$CO_2R'$ (where R' is an alkyl group, and R1 and $X^1$ are those defined above) in the presence of a base provides a compound of Formula Ie. Any relatively non-nucleophilic base can be used including carbonates, such as potassium carbonate, lithium carbonate, and sodium carbonate; bicarbonates, such as potassium bicarbonate, lithium bicarbonate, and sodium bicarbonate; potassium tert-butoxide, sodium hexamethyldisilazane, potassium hexamethyldisilazane, lithium hexamethyldisilazane, LDA, sodium hydride, or amines, such as secondary and tertiary amines; and resin bound amines such as 1,3,4,6,7,8-hexahydro-2Hpyrimido[1,2-a]pyrimidine. Conveniently, the reaction is carried out in a solvent which is relatively polar but inert under the reaction conditions, preferably an amide such as dimethyl formnalide, N-substituted pyrrolidinone, especially 1-methyl-2-pyrrolidinone, and at a temperature of about 25° C. to about 150° C.

Oxidation of Ie with an oxidizing agent, e.g. a peracid such as 3-chloroperbenzoic acid (i.e., MCPBA) or Oxone®, provides a sulfone (If) which can be converted to a variety of target compounds. Typically the oxidation of Ie is carried out in a solvent which is inert under the conditions of the oxidation. For example, when MCPBA is used as the oxidizing agent, the solvent is preferably a halogenated aliphatic hydrocarbon, especially chloroform. When Oxone® is used as the oxidizing agent, the solvent is preferably MeOH, aqueous ethanol or aqueous THF. The reaction temperature depends on the solvent used. For an organic solvent, the reaction temperature is generally at about −20° C. to about 50° C., preferably about 0° C. to about room temperature. When water is used as the solvent, the reaction temperature is generally from about 0° C. to about 50° C., preferably about 0° C. to about room temperature. Alternatively, the oxidation may be carried under catalytic conditions with rhenium/peroxide based reagents, see ("Oxidation of Sulfoxides by Hydrogen Peroxide, Catalyzed by Methyltrioxorhenium(VII)", Lahti, David W.; Espenson, James H, *Inorg. Chem.* (2000) 39(10) pp. 2164–2167; "Rhenium oxo complexes in catalytic oxidations, *Catal. Today* (2000) 55(4), pp 317–363 and "A Simple and Efficient Method for the Preparation of Pyridine N-Oxides", Coperet, Christophe; Adolfsson, Hans; Khuong, Tinh-Alfredo V.; Yudin, Andrei K.; Sharpless, K. Barry, *J. Org. Chem.* (1998) 63(5), pp 1740–1741).

Reacting the compound If with an amine ($R^3$—$NH_2$) provides the compounds of Formula I'. The reaction can be carried out in the presence or absence of solvent. Conveniently, the reaction is carried out at temperatures of from about 0° C. to about 200° C., more preferably about room temperature to about 150° C. Alternatively, in some cases rather than using the sulfone If, the sulfide Ie or the corresponding sulfoxide can be reacted directly with an amine ($R^3$—$NH_2$) to provide the compounds of Formula I'.

Accordingly, the present invention provides a method of preparing compounds of Formula I, by treating a compound of general Formula Ie, If or the corresponding sulfoxide with an amine ($R^3$—$NH_2$) and optionally reacting the resulting product with $R^2$-L, where $R^2$ is alkyl and L is a leaving group.

Scheme 2

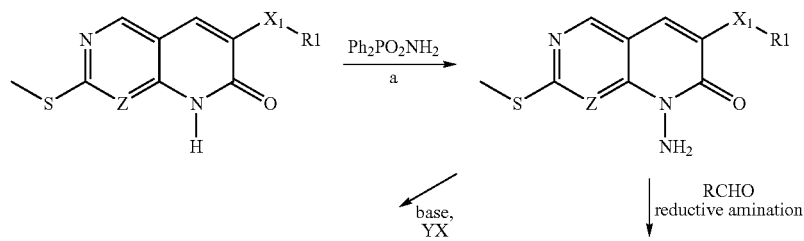

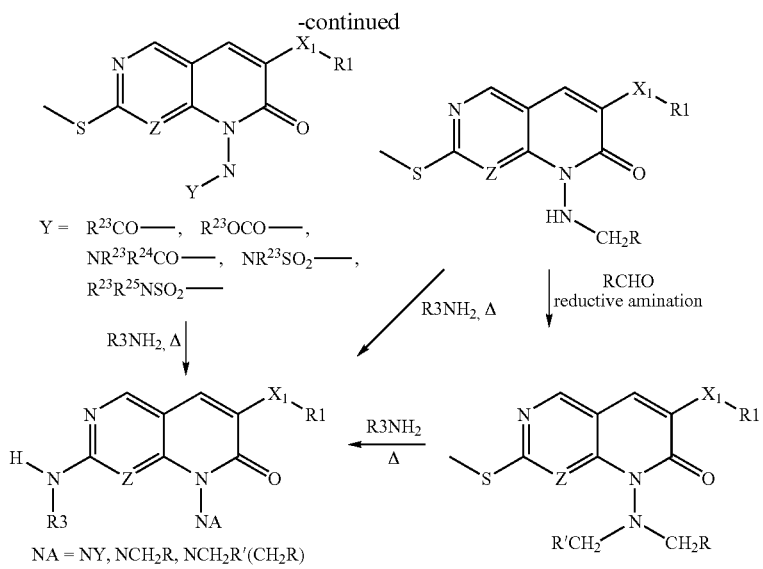

Compounds of Formula I where $R^2$ is amino, mono alkyl amino, dialkylamino or $NR^{22}$—Y—$R^{23}$ may be prepared as shown in Scheme 2 from the corresponding 2-alkylthio-8-amino-[2,3-d]pyridopyrimidin-7(8H)-one (IV, Z=N), or 7-alkylthio-1-amino-1,6-naphthyridin-2-one (IV, Z=CH) shown in Scheme 2 by amination with O-diphenylphosphinylhydroxylamine (see Colvin, E. W.; Kirby, G. W.; Wilson, A. C. *Tetrahedron Lett.* (1982), 23, 3835 for preparation and Klottzer, W.; Stadlwieser, J.; Raneburger, J. *Org. Synth.* (1986), 64, p 96–103 for examples). The resulting amine can then be substituted in a variety of different ways. Mono or di-alkylation is possible via stepwise reductive alkylations (using substituted aldehydes). Alternatively, the amine may be acylated with acyl halides, haloformates or halocarbonates. The amine can also be sulfonylated with sulfonyl halides. Finally, displacement of the sulfide (or the corresponding sulfoxide or sulfone) with an amine $R^3NH_2$ as previously described for compound Ie in Scheme 1 provides compounds of Formula I (compounds of Formula I where Z is CH and $R^2$=NA).

Ethyl 2,4-dichloropyridine-5-carboxylate is treated with an amine $R^2NH_2$ to provide ester 3g. This reaction is conveniently carried out in a solvent which is inert under the reaction conditions, preferably acetonitrile, an optionally halogenated aromatic hydrocarbon, or an open-chain or cyclic ether such as THF, a formamide or a lower alkanol. Suitably, the reaction is carried out at about −20° C. to about 120° C.

Reduction of a compound of Formula 3g provides an alcohol. This reduction is typically carried out using lithium aluminum hydride in a manner well known to those of skill in the art (e.g., in a solvent which is inert under the conditions of the reduction, preferably an open-chain or cyclic ether, especially THF, at about −20° C. to about 70° C., preferably at about 0° C. to about room temperature).

Oxidation of the alcohol provides a carboxaldehyde of Formula 3h. The oxidation is typically carried out with manganese dioxide, although numerous other methods can also be employed (see, for example, ADVANCED ORGANIC CHEMISTRY, $4^{TH}$ ED., March, John Wiley & Sons, New York

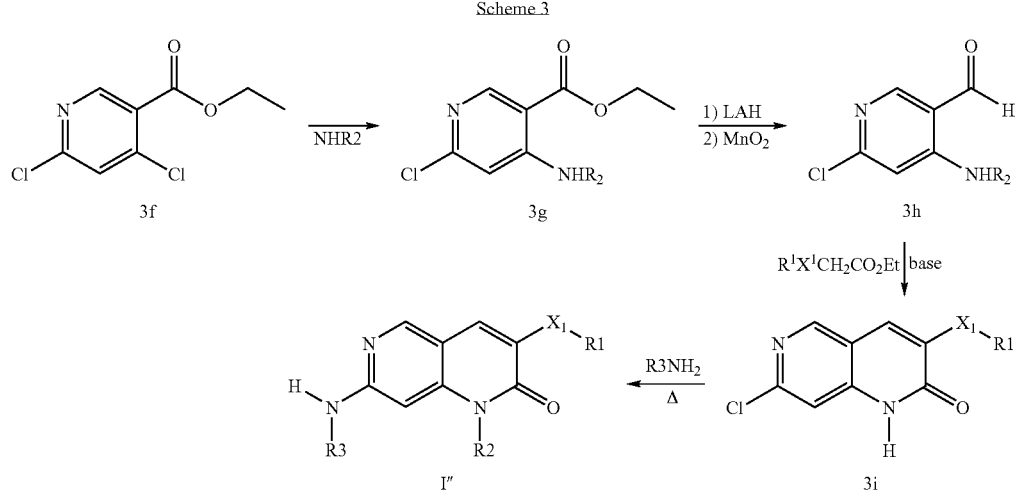

(1992)). Depending on the oxidizing agent employed, the reaction is carried out conveniently in a solvent which is inert under the specific oxidation conditions, preferably a halogenated aliphatic hydrocarbon, especially DCM, or an optionally halogenated aromatic hydrocarbon. Suitably, the oxidation is carried out at about 0° C. to about 60° C. Reaction of a carboxaldehyde of Formula 3h with an ester, $R^1$—$X^1CH_2$—$CO_2R'$ (where R' is an alkyl group, and R1 and $X^1$ are those defined above) in the presence of a base provides a compound of Formula 3i. Any relatively non-nucleophilic base can be used including carbonates, such as potassium carbonate, lithium carbonate, and sodium carbonate; bicarbonates, such as potassium bicarbonate, lithium bicarbonate, and sodium bicarbonate; potassium tert-butoxide, sodium hexamethyldisilazane, potassium hexamethyldisilazane, lithium hexamethyldisilazane, LDA, sodium hydride, or amines, such as secondary and tertiary amines; and resin bound amines such as 1,3,4,6,7,8-hexahydro-2Hpyrimido[1,2-a]pyrimidine. Conveniently, the reaction is carried out in a solvent which is relatively polar but inert under the reaction conditions, preferably an amide such as dimethyl formamide, N-substituted pyrrolidinone, especially 1-methyl-2-pyrrolidinone, and at a temperature of about 25° C. to about 150° C.

Displacement of the chloride with an amine $R^3NH_2$ as previously described for compound Ie in Scheme 1 (preferably neat at 150–160° C.) provides compounds of Formula I'' (compounds of Formula I where Z is CH).

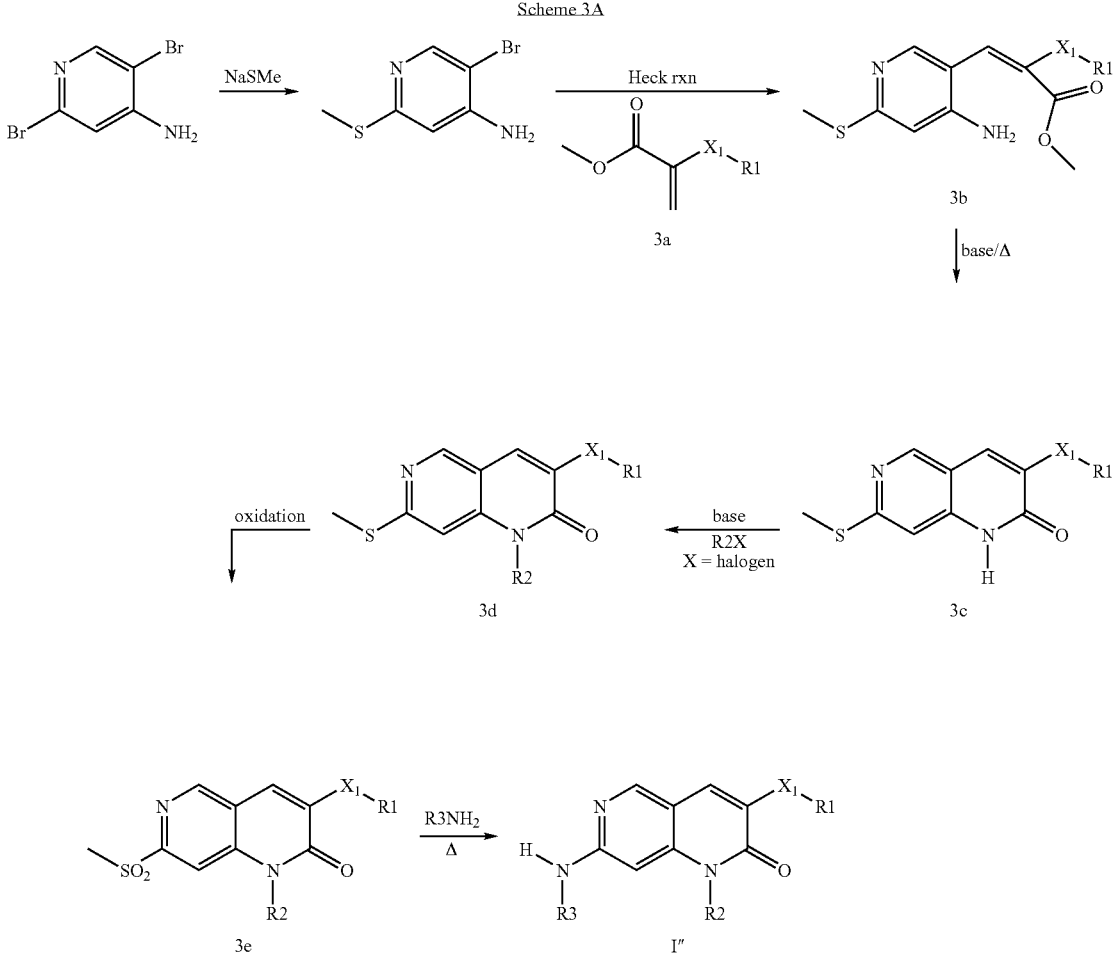

Scheme 3A 4-amino-3,6-dibromopyridine (Den Hertog et. al., Rec. Trav. Chim. Pays-Bas, 64 85–100 (1945)), is treated with sodium methyl thiolate to give 4-amino-3-bromo-6-methylthio-pyridine (Step a, see Windscheif, P; Voegtle, F.; Synthesis, 87092 (1994). The methylthiopyridine is coupled in a Heck reaction under palladium catalysis (e.g. palladium acetate) in the presence of base (e.g. potassium acetate or tributylamine) with the vinyl ester 3a to give a compound of Formula 3b (see Dong, Y.; Busacca, C. A. J. Org. Chem., 62, 6464–65 (1997). Ring closure under basic conditions gives a 1,6-naphthyridone of Formula 3c. Alkylation of 3c with an alkyl halide (or any other-alkylating agent $R^3$—X where X is a leaving group) gives a 1-alkylated naphthyridone of Formula 3d. Oxidation of 3d and displacement of the sulfone with an amine $R^3NH_2$ as previously described for compound Ie in Scheme 1 provides compounds of Formula I'' (compounds of Formula I where Z is CH). An alternative route is shown in Scheme 3A.

Scheme 4

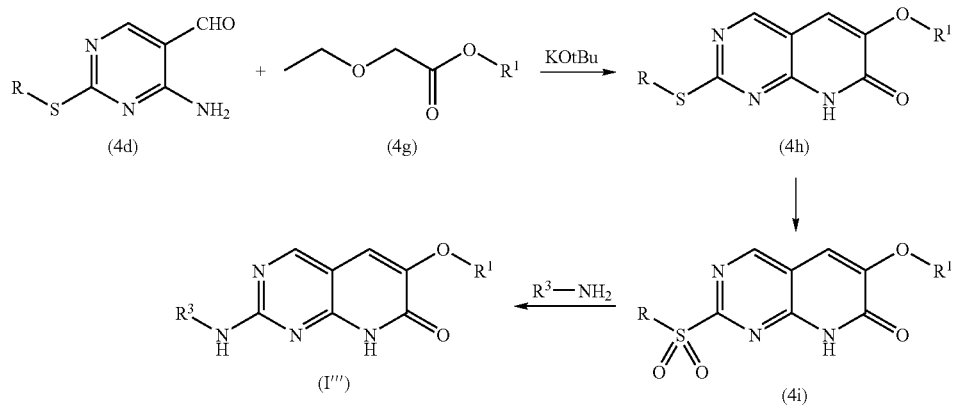

Compounds of formula (4d) can be reacted with ethyl ethoxyacetate in an appropriate solvent such as toluene, with addition of potassium t-butoxide to provide compounds of formula (4h). Compounds (4h) can be converted to the corresponding sulfonyl compounds (4i) upon reaction with oxidant or peracid such as chloroperbenzoic acid in solvent such as DCM. Compounds (4i) can be converted to compounds of Formula (I″) upon reaction with the desired amine $R^3$—$NH_2$, in a solvent such as DCE.

One of skill in the art will understand that certain modifications to the above schemes are contemplated and within the scope of the present invention. For example, certain steps will involve the use of protecting groups for functional groups that are not compatible with particular reaction conditions.

Pharmaceutical Compositions Containing the Compounds

The compounds of Formula I and the pharmaceutically acceptable salts of basic compounds of Formula I with acids can be used as medicaments, e.g., in the form of pharmaceutical preparations. The pharmaceutical preparations can be administered enterally, e.g., orally in the form of tablets, coated tablets, dragees, hard and soft gelatine capsules, solutions, emulsions or suspensions, nasally, e.g., in the form of nasal sprays, or rectally, e.g., in the form of suppositories. However, they may also be administered parenterally, e.g., in the form of injection solutions.

The compounds of Formula I and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of Formula I and their aforementioned pharmaceutically acceptable salts.

Medicaments which contain a compound of Formula I or a pharmaceutically acceptable salt of a basic compound of Formula I with an acid in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of Formula I and their aforementioned pharmaceutically acceptable salts can be used in accordance with the invention as therapeutically active substances, especially as antiinflarmmatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of Formula I and their aforementioned pharmaceutically-acceptable salts for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object of the invention.

Methods of Using the Compounds and Compositions

Compounds of Formula I would be useful for, but not limited to, the treatment of any disorder or disease state in a human, or other mammal, which is exacerbated or caused by excessive or unregulated TNF or p38 kinase production by such mammal. Accordingly, the present invention provides a method of treating a cytokine-mediated disease which comprises administering an effective cytokine-interfering amount of a compound of Formula I, or a pharmaceutically acceptable salt or tautomer thereof.

Compounds of Formula I would be useful for, but not limited to, the treatment of inflammation in a subject, and for use as antipyretics for the treatment of fever. Compounds of the invention would be useful to treat arthritis, including but not limited to, rheumatoid aithritis, spondyloarthropathies (e.g., ankylosing spondylitis), gouty arritis, psoriatic arthritis, osteoarthritis, systemic lupus erythematosus, juvenile arthritis, and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, bums, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds can further be used for preventing the production of cyclooxygenase-2.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional anti-inflammatories, such as together with steroids, cyclooxygenase-2 inhibitors, NSAMDs, DMARDS, immunosuppressive agents, 5-lipoxygenase inhibitors, LTB$_4$ antagonists and LTA$_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

Additional objects, advantages, and novel features of this invention will become apparent to those skilled in the art upon examination of the following illustrative examples thereof, which are not intended to be limiting.

Unless otherwise stated, all temperatures including melting points (i.e., Mpt.) are in degrees celsius (° C.).

Preparation 1

4-Methylamino-2-methylthiopyrimidine-5-carboxaldehyde

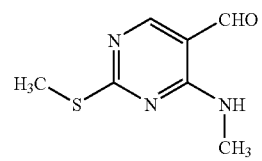

Step A: Preparation of ethyl 4-methylamino-2-methyl-thiopyrimidine-5-carboxylate

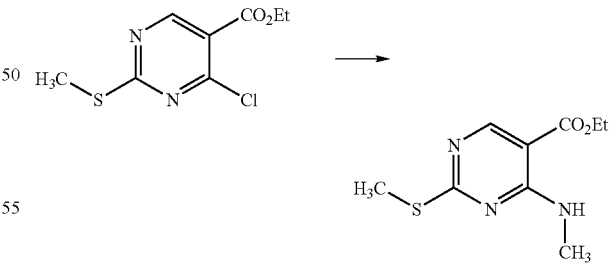

To a solution of ethyl 4-chloro-2-methylthiopyrimidine-5-carboxylate (Aldrich, 20 g, 86 mmol) in 250 mL of DCM at 0° C. was slowly added a solution of methylamine in EtOH (33%, 35 mL 281 mmol). After stirring for 30 minutes, water (150 mL) was added and the phases were separated. The organic phase was dried (MgSO$_4$) and filtered. The filtrate was evaporated under reduced pressure to give 19 g of the ethyl 4-methylamino-2-methylthiopyrimidine-5-carboxylate as a white solid.

Step B: Preparation of 4-methylamino-2-methylthiopyrimidine-5-methanol

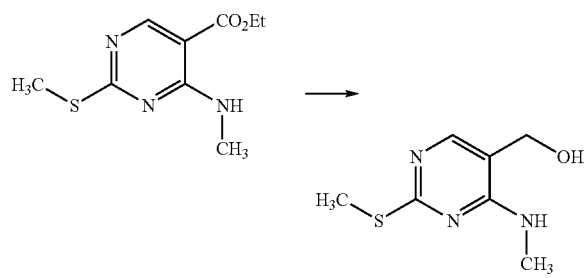

Lithium aluminum hydride (8.2 g, 215 mmol) was stirred in dry THF (300 mL) at 5° C. and treated dropwise with a solution of ethyl 4-methylamino-2-methylthio-pyrimidine-5-carboxylate (46 g, 215 mmol) in dry THF (450 mL). The reaction mixture was stirred for 15 minutes and then water (18 mL) was added dropwise with caution. The reaction was stirred for 30 minutes and then an aqueous solution of sodium hydroxide (15%, 8.5 mL) was added dropwise, followed by water (25.5 mL). The resulting suspension was stirred for 17 hours at room temperature and then filtered. The filter residue was washed with THF (2x, 100 mL) and the combined filtrate and washings were evaporated under reduced pressure. The residue was suspended in EtOAc/hexane—½ (200 mL) and the solid was filtered and dried to provide 32.7 g of 4-methylamino-2-methylthiopyrimidine-5-methanol as a yellow solid.

Step C: Preparation of 4-methylamino-2-methylthiopyrimidine-5-carboxaldehyde

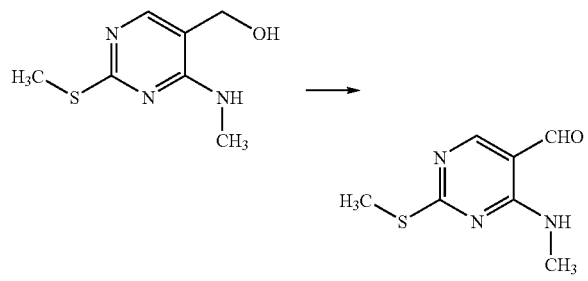

4-Methylamino-2-methylthiopyrimidine-5-methanol (20 g, 108 mmol) and 1 L of DCM were combined with stirring and treated with manganese dioxide (87 g, 1 mol). The resulting suspension was stirred for 24 hours and then filtered through celite. The filter residue was washed with DCM (100 mL), and the combined filtrate and washings were evaporated under reduced pressure to give 15.8 g of the 4-methylamino-2-methylthiopyrimidine-5-carboxaldehyde as a white solid.

Preparation 2

4-(Cyclopropylamino)-2-(methylthio)pyrimidine-5-carboxaldehyde

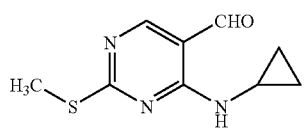

4-cyclopropylamino-2-methylthiopyrimidine-5-carboxaldehyde was prepared as described in Example 1 (steps A through C) starting with ethyl 4-chloro-2-methylthiopyrimidine-5-carboxylate (Aldrich Chemical Co.) and cyclopropyl amine (Aldrich Chemical Co.).

Preparation 3

4-[(4-Fluorophenyl)amino]-2-(methylthio)pyrimidine-5-carboxaldehyde

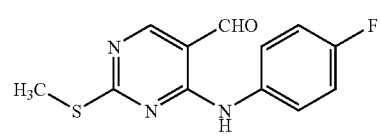

4-[(4-fluorophenyl)amino]-2-(methylthio)pyrimidine-5-carbaldehyde was prepared as described in Example 1 (steps A through C) starting with ethyl 4-chloro-2-methylthiopyrimidine-5-carboxylate (Aldrich Chemical Co.) and 4-fluoroaniline (Aldrich Chemical Co.).

Preparation 4

4-(Ethylamino)-2-(methylthio)pyrimidine-5-carboxaldehyde

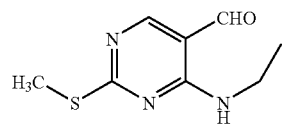

Step A: Preparation of ethyl 4-ethylamino-2-methyl-thiopyrimidine-5-carboxylate

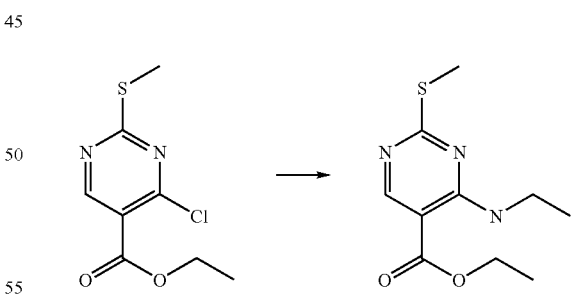

To a solution of 25-g (107 mmole) ethyl 4-chloro-2-methylthio-5-pyrimidinecarboxylate in 250 ml of THF was added 47 ml (337 mmole) triethylamine and 43 ml of 70% ethylamine solution (668 mmole). The mixture was stirred at room temperature for 4 hours and evaporated to dryness. This material was dissolved in a mixture of EtOAc/water, washed twice with 10% NaHCO$_3$ solution, dried (MgSO$_4$), and evaporated to dryness to give the above-titled product as a solid. Yield 24.1 g.

Step B: Preparation of 4-ethylamino-2-methylthiopyrimidine-5-methanol

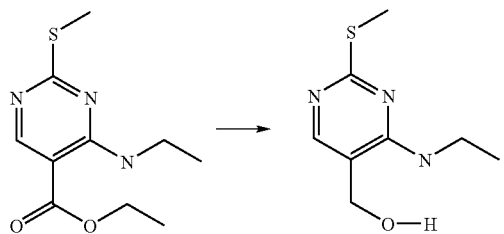

A solution of the ethyl 4-ethylamino-2-methylthio-pyrimidinecarboxylate (24.1 g, 100 mmole) in THF (250 ml) was cooled in an ice bath to 0° C. To this solution was carefully added in small portions over an hour lithium aluminum hydride (4.3 g, 113 mmole). One hour after addition was complete, water was slowly added (4.3 ml), then to this was added a solution of NaOH (4.3 ml, 15%), then an additional 13 ml of water, and then the mixture was stirred for 1 hour. The resulting suspension was filtered and the filter residue washed twice with 100 ml of THF. This solution was evaporated under reduced pressure. The residue was stirred with 150 ml Et$_2$O, filtered and dried. Yield 19.1 g.

Step C: Preparation of 4-ethylamino-2-methylthiopyrimidine-5-carboxaldehyde

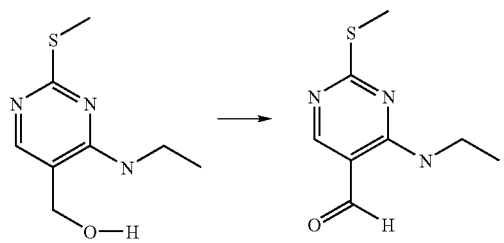

To a solution of 4-ethylamino-2-methylthiopyrimidine-5-methanol (19.1 g, 96 mmole) in 1000 ml of DCM was added 87 g of manganese dioxide. The resulting suspension was stirred for 20 hours and filtered through celite. The residue was washed twice with 100 ml of DCM, and the combined filtrate and washings were evaporated under reduced pressure to give the product as a solid. Yield 12.8 g.

Preparation 5

4-Amino-2-methylthiopyrimidine-5-carbaldehyde

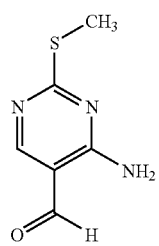

Step A: Preparation of 3,3-Diethoxy-2-formylpropionitrile Potassium Salt (P-5A))

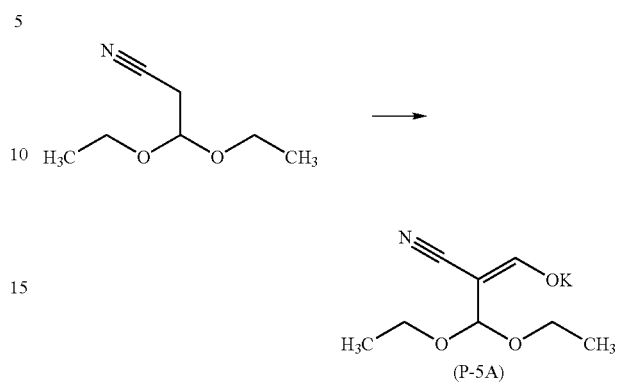

To a stirred solution of 3,3-diethoxypropane-nitrile (283.80 g, 1.98 moles) and methyl formate (148.80 g, 2.48 moles) in anhydrous THF (1.1 L) at 10° C. was added 1.0 M potassium tert-butoxide in THF (2.2 L, 2.2 moles). The temperature was maintained in the range of 10° C. to 15° C. throughout the 45 minute addition. Following the addition, the resulting slurry was stirred for 2 hours at ambient temperature. Hexane (400 mL) was then added and stirring was continued for another 20 min. The slurry was filtered and the cake washed with 1/1 hexanes/THF and dried overnight at 60° C. in a vacuum oven to yield 302.5 grams (73.0%) of the above compound P-5A as a pale tan powder. $^1$H-NMR (CD$_3$OD) was consistent with the desired structure.

Step B: Preparation of 4-Amino-2-sulfanylpyrimidine-5-carbaldehyde (P-5B))

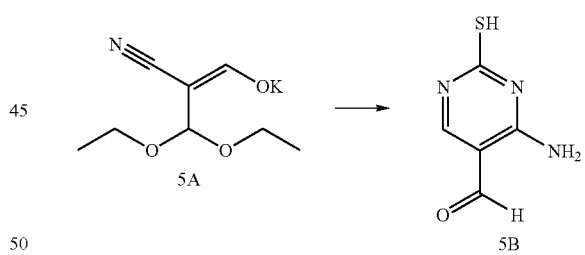

A slurry of thiourea (92.8 g, 1.22 moles) in EtOH (90 mL) was heated under reflux and vigorously stirred. To this slurry was added a suspension of 3,3-diethoxy-2-formylpropionitrile potassium salt (P-5A) (222.20 g, 1.06 moles) in 25% sodium methoxide/MeOH (85.5 mL, 0.37 mole) and EtOH (285 mL) in five aliquots over a 10 minute period, while maintaining reflux conditions (alternatively, the latter slurry may be heated to 50° C. to give a homogenous solution for the addition). An additional portion of EtOH (150 mL) was added to facilitate stirring. The thick slurry became a bright yellow color following the addition and was held under reflux for an additional 1 hour. The mixture was then cooled and evaporated to near dryness on a rotoevaporator. The residue was dissolved in water (940 mL). Crude product was precipitated from solution by the addition of 30% acetic acid (280 mL) and isolated via filtration using a medium frit sintered glass filtration funnel. The cake was washed with water (800 mL). Purification via trituration in hot water (1 L) for 30 minutes, followed by cooling and filtration gave 118.9 grams (72.3%) of product as a bright yellow solid after drying overnight at 60° C. in a vacuum oven (subsequent preparations have demonstrated that this trituration is unnecessary). An HPLC gave purity as 98.67%. $^1$H-NMR (DMSO-d$_6$) was consistent with the above desired structure (P-5B).

Step C: Preparation of 4-Amino-2-methylthiopyrimidine-5-carbaldehyde

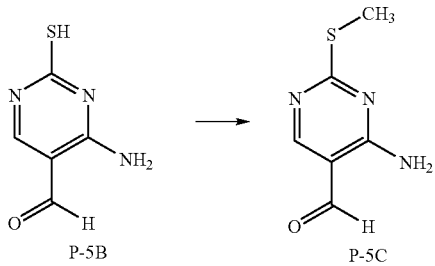

To a solution of 4-amino-2-sulfanyl-pyrimidine-5-carbaldehyde (P-5B) (100.00 g, 644.4 mmoles) and 325 mesh potassium carbonate (178.10 g, 1.29 moles) in acetone (1.5 L) was added iodomethane (128.10 g, 902.2 mmoles) dropwise over 20 minutes with mild cooling. The mixture was stirred at ambient temperature over the weekend. TLC showed remaining product (P-5B) from Step B, and then an additional aliquot of iodomethane was added (8 mL) and stirring continued overnight. TLC again showed some product from step B (P-5B) remaining and an addition portion of iodomethane was added (8 mL) and stirring was continued another 24 hour period. An HPLC showed 95.9% S-alkylated product and 3.7% of compound (P-5B). The reaction mixture was stripped to near dryness on a rotoevaporator. Water (1 L) was added to the residue and the product was collected via filtration and washed with water (200 mL). The product was dried overnight in a vacuum oven at 60° C. Yield was 103.37 grams (94.8%). HPLC showed 95.8% Preparation 5 and 4.2% of compound (P-5B).

Preparation 6

4-Amino-2-n-butylthiopyrimidine-5-carbaldehyde

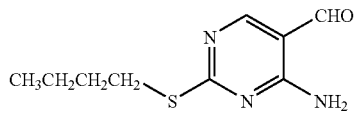

4-Amino-2-(n-butylthio)pyrimidine-5-carbaldehyde was prepared as described for Preparation 5 (steps A through C) substituting iodobutane (Aldrich Chemical Co.) for iodomethane (Aldrich Chemical Co.) in step C.

Example 1

6-Ethoxy-2[3-methoxy-1(2-methoxy-ethyl)-propylamino]-8,8a-dihydro-4aH-pyrido[2,3-d]pyrimidin-7-one

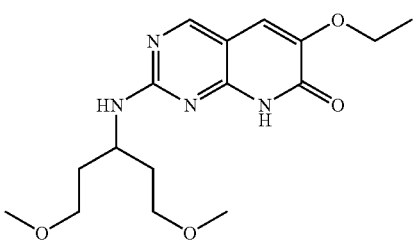

Step A: 2-Butylsulfanyl-6-ethoxy-8,8a-dihydro-4aHpyrido[2,3-d]pyrimidin-7-one

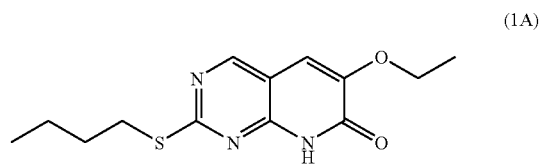

(1A)

4-Amino-2-butylsulfanyl-4,5-dihydro-pyrimidine-5-carbaldehyde (3 g, 14.2 mmol, furnished by scaleup) and ethyl ethoxyacetate (2.34 g, 2.4 ml, 17.75 mmol) were stirred in 80 ml toluene at 0°-5° C. under nitrogen. Potassium t-butoxide (1.75 g, 15.6 mmol) was added gradually. The mixture was stirred to ambient temperature, and then to 65° C. for 48 hours. An additional 20 ml of toluene and 2.4 ml ethyl ethoxyacetate were added and the reaction was maintained at 65° C. over the weekend. The reaction mixture was concentrated in vacuo and triturated with EtOAc to remove the remaining starting aldehyde. The remaining solid was further triturated with chloroform to remove additional impurities. 3.66 g of 2-Butylsulfanyl-6-ethoxy-8,8a-dihydro-4aHpyrido[2,3-d]pyrimidin-7-one (1A) of a purity greater than 80% as judged by MS/HPLC and NMR was collected.

Step B: 2-(Butane-1-sulfonyl)-6-ethoxy-8H-pyrido[2,3-d]pyrimidin-7-one

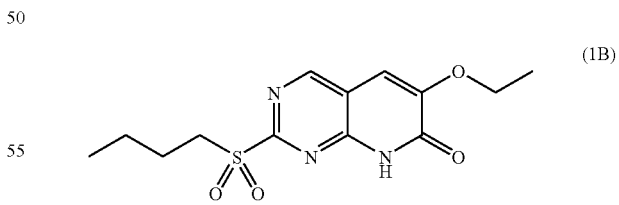

(1B)

A solution of compound (1A) (3 g, 10.7 mmol) suspended in 40 ml of DCM was cooled to 0°–5° C. in an ice bath and meta chloroperbenzoic acid (5.5 g, 32.3 mmol) was added gradually. This mixture was allowed to stir to ambient temperature overnight and then concentrated in vacuo. The residue was triturated with EtOAc and purified by column chromatography eluting with CH$_2$Cl$_2$:MeOH:actone (96:2:2) to yield 1 g of 2-(Butane-1-sulfonyl)-6-ethoxy-8H-pyrido[2,3-d]pyrimidin-7-one (3B).

Step C: 6-Ethoxy-2[3-methoxy-1 (2-methoxy-ethyl)-propylamino]-8,8a-dihydro-4aH-pyrido[2,3-d]pyrimidin-7-one A solution of compound 3B (50 mg, 0.16 mmol) and 3-methoxy-1-(2-methoxy-ethyl)-propylamine (140 mg, 0.96 mmol) in 1 ml DCE was heated to 85° C. for 72 hours. The reaction mixture was chromographed directly on a Supelco™ 2 g/12 ml silica column with gradient solvent of CH$_2$Cl$_2$ to a final solvent mixture of CH$_2$Cl$_2$:MeOH:acetone (94:3:3). Two additional chromatographies were required to provide 24 mg of 6-Ethoxy-2[3-methoxy-1 (2-methoxy-ethyl)-propylamino]-8,8a-dihydro-4aH-pyrido[2,3-d]pyrimidin-7-one (Example 1) at 86% purity as judged by MS/HPLC. M$^+$+337.

Example 2

6-Methoxy-8-methyl-2-(tetrahydro-pyran-4-ylamino)-8H-pyrido[2,3-d]pyrimidin-7-one Step A:

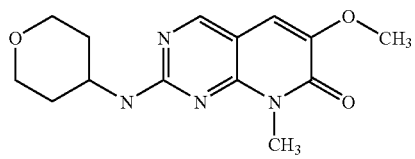
(2A)

4-Methylamino-2-methylthio-5-pyrimidinecarboxaldehyde (2 g, 10.9 mmol), methyl methoxyacetate (1.6 mL, 16.4 mmol), potassium carbonate (2.26 g, 16.4 mmol), and NMP (40 mL) were stirred at 120° C. for 66 h. The reaction mixture was cooled to room temperature, poured into water (300 mL), and extracted with EtOAc (3×100 mL). The organic layer was washed with water and brine, dried over magnesium sulfate, and concentrated in vacuo. The residue was purified by flash chromatography eluting with 20–50% acetone/hexanes to afford 502 mg of compound (2A).

Step B:

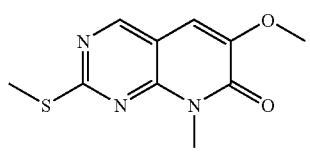
(2B)

A mixture of compound (2A) (450 mg, 1.90 mmol), 72% mCPBA (1.36 g, 5.69 mmol), and methylene chloride (100 ml) was stirred at room temperature for 3 h. An aqueous solution of sodium bisulfite (10%, 100 ml) was added to the reaction mixture and stirred at room temperature for 1 h before extraction with EtOAc (200 ml). The organic layer was washed with sat'd aqueous sodium bicarbonate, water, and brine, dried over magnesium sulfate, and concentrated in vacuo. The residue was purified by flash chromatography eluting with 0–3% MeOH/DCM to afford 235 mg of the above-titled compound (2B).

Step C: Example 2

A mixture of compound (2B) (50 mg, 0.186 mmol), 4-aminotetrahydropyran (38 mg, 0.371 mmol), and NMP (1 ml) was stirred at 80° C. for 66 h. The reaction mixture was cooled to room temperature and purified by flash chromatography (1–5% MeOH/DCM) to afford 47 mg of (4a). The free base was dissolved in MeOH, treated with 1 eq 1N HCl/Et$_2$O, and concentrated in vacuo to afford the above-titled Example 2 as the hydrochloride salt (44 mg).

Example 3

6-Ethoxy-8-methyl-2-(tetrahydro-pyran-4-ylamino)-8H-pyrido[2,3-d]pyrimidin-7-one

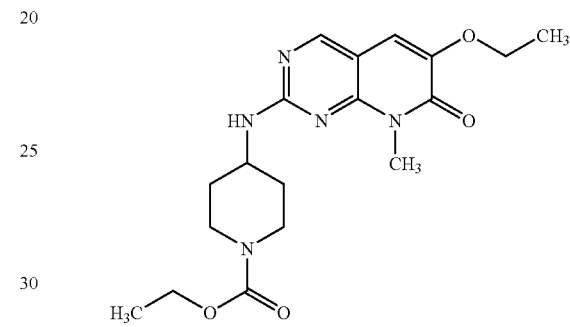

Step A:

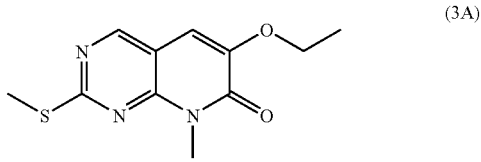
(3A)

4-Methylamino-2-methylthio-5-pyrimidinecarboxaldehyde (3 g, 16.4 mmol), ethyl ethoxyacetate (3.3 mL, 24.6 mmol), potassium carbonate (3.4 g, 24.6 mmol), and NMP (50 mL) were stirred at 120° C. for 18 h. The reaction temperature was lowered to 80° C. for 66 h, then returned to 120° C. for 18 h after a second addition of ethyl ethoxyacetate and potassium carbonate in the amounts above. The reaction mixture was poured into water (300 mL) and stirred at room temperature for 1 h. The precipitate was collected by filtration, washed with water and hexanes, and dried in vacuo to afford 2.14 g of compound (3A).

Step B:

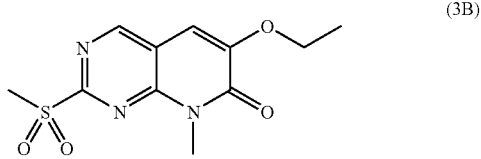
(3B)

A mixture of compound (3A) (2 g, 7.96 mmol), 72% mCPBA (5.7 g, 23.9 mmol), and methylene chloride (100 ml) was stirred at room temperature for 1 h. An aqueous solution of sodium bisulfite (10%, 100 ml) was added to the reaction mixture and stirred at room temperature for 15 min. before extraction with EtOAc (200 ml). The organic layer was washed with saturated aqueous sodium bicarbonate, water, and brine, dried over magnesium sulfate, and concentrated in vacuo to afford 1.45 of compound (3B).

Step C: Example 3

A mixture of (3B) (100 mg, 0.353 mmol), ethyl 4-amino-1-piperidinecarboxylate (0.12 mL, 0.706 mmol), and NMP (3 ml) was stirred at 120° C. for 18 h. The reaction mixture was cooled to room temperature and partitioned with water and EtOAc. The organic layer was washed with water and brine, dried over magnesium sulfate, and concentrated in vacuo. The residue was dissolved in MeOH and DCM, treated with 1N HCl/Et$_2$O (0.35 mL), and concentrated in vacuo. The resulting solids were washed with ethyl ether and dried in vacuo to afford 56 mg of the hydrochloride salt of Example 3.

Example 4

6-Ethoxy-8-methyl-2-(piperidin-4-ylamino)-8H-pyrido[2,3-d]pyrimidin-7-one

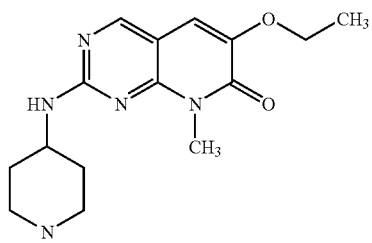

Step A: Preparation of 6-(2,6-difluorophenoxy)-8-methyl-2-(methylthio)pyrido[2,3-d]pyrimidin-7(8H)-one (4A)

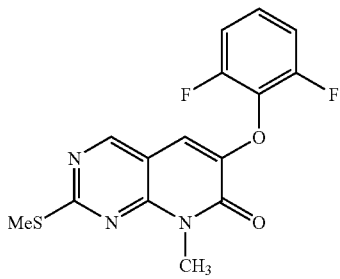

To a mixture of 4-methylamino-2-methylthiopyrimidine-5-carboxaldehyde (Preparation 1) (4.8 g, 26.2 mmol) and methyl 2,6-difluorophenoxyacetate (prepared as in Preparation 4, using 2,6-difluorophenol, 5.9 g, 32 mmol) in 50 mL of 1-methyl-2-pyrrolidinone was added potassium carbonate (6.0 g, 43.5 mmol). The reaction mixture was heated to 120° C. and after 12 hours, additional phenoxyacetate (2×, 2.0 g, 10.8 mmol) and potassium carbonate (2.0 g, 15 mmol) were added. After 6 hours of stirring at 120° C., the reaction was cooled to room temperature and water (70 mL) was added. The solution was stirred for 30 minutes and filtered. The resultant solid was washed with water (2×), EtOAc, and ether. The solid was then dried yielding 7.0 g of the above-titled sulfide (mass spec. M+1=336, MP=247–250.7° C.).

Step B. Preparation of 6-(2,6-difluorophenoxy)-8-methyl-2-(methylsulfonylpyrido[2,3-d]pyrimidin-7(8H)-one (4B)

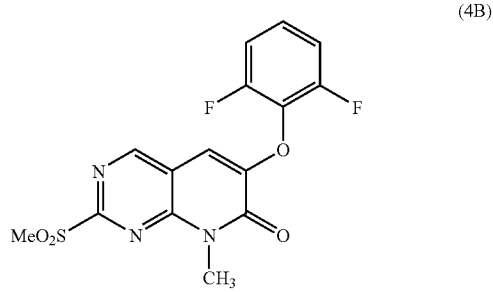

Compound 4A (7.0 g, 20.8 mmol) was dissolved in 50 mL of methylene chloride, and 3-chloroperbenzoic acid (77%, 11.5 g, 51.5 mmol) was added. The mixture was stirred at room temperature for 16 hours, filtered, then washed with aqueous sodium sulfite solution (2×, 75 mL) followed by saturated aqueous sodium bicarbonate solution (3×, 75 mL). The organic solution was then dried (brine, Na$_2$SO$_4$) and evaporated. The resultant solid was stirred with ether for 1 hour and filtered to yield 5.5 g of the above-titled sulfone 4B (mass spec. M+1=368, MP=215.2–216.4° C.).

Step C: Preparation of ethyl 4-{[6-(2,6-difluorophenoxy)-8-methyl-7-oxo-7,8-dihydropyrido[2,3-d]pyrimidin-2-yl]amino}piperidine-1-carboxylate (4C)

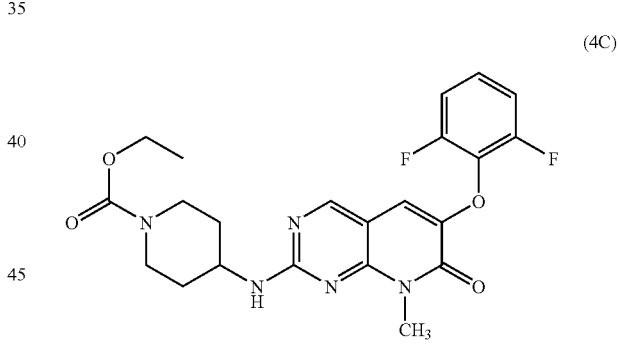

A mixture of compound 4B (1.0 g, 2.7 mmol) and ethyl 4-amino-1-piperidinecarboxylate (0.93 ml, 5.4 mmol) in 5 mL 1-methyl-2-pyrrolidinone was stirred at 100° C. for 1 hour and then cooled to room temperature. The reaction slurry was added to 20 ml distilled water, and the yellow precipitate was collected by vacuum filtration and subsequently dried in vacuo to yield 1.28 g of compound 4C. About 80 mg of this product was dissolved in MeOH (1–2 mL) and then treated with hydrochloric acid in ether (1M). Evaporation of the organics, followed by addition of ether (1–2 mL) yielded a solid. Isolation of this solid via filtration and drying provided 66 mg of Compound 4C as the hydrochloride salt (MP=197–204° C.).

Step D: 6-Ethoxy-8-methyl-2-{[(1-methanesulfonyl)piperidiny-4-yl]amino}pyrido[2,3-d]pyrimidin-7(8H)one (Example 4)

A mixture of ethyl 4-{[6-(2,6-difluorophenoxy)-8-methyl-7-oxo-7,8-dihydropyrido[2,3-d]pyrimidin-2-yl]

amino}piperidine-1-carboxylate from Step C (1.2 g, 2.52 mmol) and potassium hydroxide (2.83 g, 50.4 mmol) in 20 mL of EtOH was refluxed for 48 hours, and then the reaction solvent was evaporated under reduced pressure. The residue was taken up in 100 ml water and chilled in an ice bath before acidifying with dropwise addition of concentrated HCl. The acidic aqueous solution was then extracted with DCM (2×). The aqueous solution was then cooled in an ice bath and re-alkalized with sodium hydroxide. The alkaline solution was then extracted with DCM (2×). The organic extracts from the alkaline aqueous solution were combined, dried with magnesium sulfate, concentrated and dried in vacuo to yield 92 mg of crude product.

Alternative Method of Preparation for Example 4

Alternatively, Example 4 was prepared from a mixture of the free base of Example 3 (prepared as described above, 358 mg, 0.954 mmol), potassium hydroxide (1.07 g, 19.1 mmol), and EtOH (10 mL), which was refluxed for 5 days. The reaction mixture was concentrated in vacuo. The residue was dissolved in water, acidified with 2N HCl, and extracted with DCM. The aqueous layer was made alkaline with saturated aqueous sodium bicarbonate and re-extracted with DCM (2×100 mL). The combined organic extracts from the alkaline solution were dried over magnesium sulfate and concentrated in vacuo to afford 24 mg of Example 4. A portion of Example 4 (3 mg) was dissolved in MeOH, treated with 1 eq 1N HCl/Et2O, and concentrated in vacuo to afford 4 mg of the hydrochloride salt of Example 4.

Example 5

6-Ethoxy-8-methyl-2-{[(1-methanesulfonyl)piperidiny-4-yl]amino}pyrido[2,3-d]pyrimidin-7(8H)-one

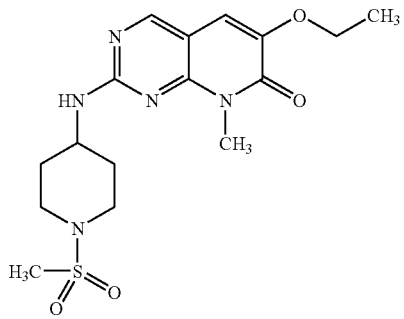

The crude piperidine product from Example 4 (0.92 g, 0.237 mmol) was taken up in 5 mL DCM with sodium carbonate (0.050 g, 0.475 mmol) and methanesulfonyl chloride (0.022 mL, 0.285 mmol) and stirred at room temperature for 17 hours. An additional aliquot of methane sulfonyl chloride (0.040 mL) and sodium carbonate (50 mg) were added, and the reaction was stirred at room temperature for 24 hours. A final aliquot of methane sulfonyl chloride (0.080 mL) and sodium carbonate (150 mg) was added and the reaction was stirred at room temperature for 48 hours. All starting material was consumed and the organic layer was washed with water, dried with magnesium sulfate, and concentrated in vacuo to an oil. The reaction mixture was purified by column chromatography (SiO$_2$, CH$_2$Cl$_2$/MeOH— gradient from 0.5/99.5 to 3/97). The column fractions were combined and concentrated under reduced pressure to provide the desired product (25 mg). The product was dissolved in EtOAc (1–2 mL) and then treated with hydrochloric acid in ether (1M, 1 eq). Isolation of the solid by rinsing with ether, filtration, and drying in vacuo provided 19 mg of Example 5 as the hydrochloride salt (MP=219.56–221.2° C.).

Alternative Method of Preparation for Example 5

A mixture of Example 4 (21 mg, 0.069 mmol), sodium carbonate (15 mg, 0.138 mmol), methanesulfonyl chloride (0.06 mL), and DCM (10 ml) was stirred at room temperature for 18 h. The reaction mixture was poured into water (100 mL) and extracted with DCM (2×100 mL). The combined organic extracts were dried over magnesium sulfate and concentrated in vacuo. The dry residue was dissolved in MeOH, treated with 1N HCl/Et$_2$O, and concentrated in vacuo. The resulting solids were washed with Et$_2$O and dried in vacuo to afford 15 mg of Example 5 as the hydrochloride salt.

Example 6

This example illustrates a p38 (MAP) kinase in vitro assay useful for evaluating the compounds of the present invention.

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn et al., *J. Biol. Chem.*, 266:4220–4227 (1991).

The phosphorylated form of the recombinant p38 MAP kinase was co-expressed with SEK-1 and MEKK in *E. Coli* (see, Khokhlatchev, et al., *J. Biol. Chem.* 272:11057–11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

The IC$_{50}$ value was defined as the concentration of the test compound corresponding to half-maximal reduction in 450 nm absorbance. Compounds according to the invention as described herein were tested in this assay and found to have a measurable level of activity for inhibiting p38.

Example 7

This example illustrates an in vitro assay to evaluate the inhibition of LPS-induced TNF-α production in THP 1 cells.

The ability of the compounds of this invention to inhibit the TNF-α release was determined using a minor modification of the methods described in Blifeld, et al. *Transplantation*, 51:498–503 (1991).

(a) Induction of TNF Biosynthesis:
THP-1 cells were suspended in culture medium [RPMI (Gibco-BRL, Gailthersburg, Md.) containing 15% fetal bovine serum, 0.02 mM 2-mercaptoethanol], at a concentration of 2.5×10⁶ cells/mL and then plated in 96 well plate (0.2 mL aliquots in each well). Test compounds were dissolved in DMSO and then diluted with the culture medium such that the final DMSO concentration was 5%. Twenty five µL aliquots of test solution or only medium with DMSO (control) were added to each well. The cells were incubated for 30 min., at 37° C. LPS (Sigma, St. Louis, Mo.) was added to the wells at a final concentration of 0.5 µg/ml, and cells were incubated for an additional 2 h. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNF-α antibodies (2TNF-H12 and 2TNF-H34) described in Reimund, J. M., et al. *GUT*. Vol. 39(5), 684–689 (1996).

Polystyrene 96-well plates were coated with 50 µl per well of antibody 2TNF-H$_{12}$ in PBS (10 µg/mL) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/nL followed by 6 half log serial dilutions.

Twenty five µL aliquots of the above culture supernatants or TNF standards or only medium (control) were mixed with 25 µL aliquots of biotinylated monoclonal antibody 2TNF-H34 (2 µg/mL in PBS containing 0.1% BSA) and then added to each well. The samples were incubated for 2 hr at room temperature with gentle shaking and then washed 3 times with 0.1% BSA in PBS. 50 µl of peroxidase-streptavidin (Zymed, S. San Francisco, Calif.) solution containing 0.416 µg/mL of peroxidase-streptavidin and 0.1% BSA in PBS was added to each well. The samples were incubated for an additional 1 hr at room temperature and then washed 4 times with 0.1% BSA in PBS. Fifty µL of O-phenylene-diamine solution (1 µg/mL O-phenylene-diamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

The IC$_{50}$ value was defined as the concentration of the test compound corresponding to half-maximal reduction in 450 nm absorbance.

Example 8

This example illustrates an in vivo assay to evaluate the inhibition of LPS-induced TNF-α production in mice (or rats).

The ability of the compounds of this invention to inhibit the TNF-α release, in vivo, is determined using a minor modification of the methods described in described in Zanetti, et. al., *J. Immunol.*, 148:1890 (1992) and Sekut, et. al., *J. Lab. Clin. Med.*, 124:813 (1994).

Female BALB/c mice weighing 18–21 grams (Charles River, Hollister, Calif.) are acclimated for one week. Groups containing 8 mice each are dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice are injected intraperitoneally with 20 µg of LPS (Sigma, St. Louis, Mo.). After 1.5 h, the mice are sacrificed by CO$_2$ inhalation and blood was harvested by cardiocentesis. Blood is clarified by centrifugation at 15,600×g for 5 min., and sera are transferred to clean tubes and frozen at −20° C. until analyzed for TNF-α by ELISA assay (Biosource International, Camarillo, Calif.) following the manufacturer's protocol.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A method for treating a p38 mediated disorder comprising:

administering to a patient in need of such treatment, an effective amount of a compound of Formula I

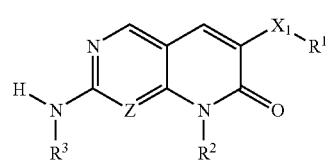

Formula I or a pharmaceutically acceptable salt thereof, wherein:

Z is CH;

$X^1$ is O, $NR^4$ (where $R^4$ is hydrogen or alkyl), S or C=O;

$R^1$ is alkyl, cycloalkyl, cycloalkylalkyl or —CH$_2$-alkenyl;

$R^2$ is hydrogen, alkyl, cycloalkyl, cycloalkylalkyl, aryl, aralkyl, haloalkyl, heteroalkyl, cyanoalkyl, alkylene-C(O)—$R^{21}$ (where $R^{21}$ is hydrogen, alkyl, hydroxy, alkoxy, amino, monoalkylamino or dialkylamino), amino, monoalkylamino, dialkylamino, acyl, or $NR^{22}$—Y—$R^{23}$ (where Y is —C(O), —C(O)O—, —C(O)NR$^{24}$, S(O)$_2$ or S(O)$_2$NR$^{25}$; $R^{22}$, $R^{24}$ and $R^{25}$ are independently hydrogen or alkyl; and $R^{23}$ is hydrogen, alkyl, cycloalkyl, cycloalkylalkyl, heteroalkyl or optionally-substituted phenyl); and $R^3$ is alkyl, haloalkyl, aryl, aralkyl, heteroaryl, heteroaralkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl, or -heterocycloamino-$SO_2$—$R^{12}$ (where $R^{12}$ is haloalkyl, aryl, aryalkyl, heteroaryl or heteroaralkyl).

2. The method of claim 1, wherein said p38 mediated disorder is Alzheimer's disease.

3. The method of claim 1, wherein $X^1$ is —O—.

4. The method of claim 3, wherein $R^1$ is alkyl or cycloalkyl.

5. The method of claim 4, wherein $R^3$ is cycloalkyl, cycloalkylalkyl, heteroalkylsubstituted cycloalkyl, heterosubstituted cycloalkyl, heteroalkyl, heterocyclyl or heterocyclylalkyl.

6. The method of claim 4, wherein $R^3$ is cycloalkyl, heteroalkylsubstituted cycloalkyl, heterosubstituted cycloalkyl, heteroalkyl or heterocyclyl.

7. The method of claim 4, wherein $R^3$ is optionally-substituted heterocyclyl.

8. The method of claim 4, wherein $R^3$ is hydroxyalkyl or alkoxyalkyl.

9. The method of claim 4, wherein $R^2$ is hydrogen, alkyl, aryl, cycloalkyl or heteroalkyl.

10. The method of claim 4, wherein $R^2$ is alkyl or hydroxyalkyl.

* * * * *